United States Patent
Pfeiffer et al.

(10) Patent No.: US 6,394,961 B1
(45) Date of Patent: May 28, 2002

(54) METHOD TO INCREASE TRANSPULMONARY THERMODILUTION CARDIAC OUTPUT ACCURACY BY USE OF EXTRAVASCULAR THERMOVOLUME TO CONTROL THE AMOUNT OF THERMAL INDICATOR

(75) Inventors: Ulrich J. Pfeiffer; Thorsten Burger, both of Munich (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/697,600

(22) Filed: Oct. 27, 2000

Related U.S. Application Data
(60) Provisional application No. 60/161,931, filed on Oct. 28, 1999.

(51) Int. Cl.[7] ............................... A61B 5/02; A61B 5/00
(52) U.S. Cl. ........................ 600/526; 600/505; 600/549
(58) Field of Search ................................. 600/526, 505, 600/549

(56) References Cited

U.S. PATENT DOCUMENTS

| | | |
|---|---|---|
| 3,359,974 A | 12/1967 | Khalil |
| 3,651,319 A | 3/1972 | Czekajewski |
| 3,726,269 A | 4/1973 | Webster, Jr. |
| 3,915,155 A | 10/1975 | Jacobson et al. |
| 4,217,910 A | 8/1980 | Khalil |
| 4,230,126 A * | 10/1980 | Elings .......................... 600/484 |
| 4,236,527 A | 12/1980 | Newbower et al. |
| 4,240,441 A | 12/1980 | Khalil |
| 4,507,974 A | 4/1985 | Yelderman |
| 4,595,015 A | 6/1986 | Jansen et al. |
| 4,819,655 A | 4/1989 | Webler |
| 5,435,308 A | 7/1995 | Gallup et al. |

OTHER PUBLICATIONS

Saadjian A. et al., "Cardia Output Measurement by Thermodilution" *Medical Progress Technology*, vol. 3, No. 4, 1976, pp. 161–167, XP002160218, West Germany, p. 164, right–hand column, line 19–22 abstract.
WO 9321823 (Nov. 11, 1993) "Process for Determining the Fill Level of a Circulatory System of a Patent".
PCT /EP 00/10590 (Oct. 27, 2000) "Apparatus, Computer System and Computer Program for Determining a Cardio-Vascular Parameter of a Patient" claiming priority of US Provisional Appln. No. 60/161,931.

* cited by examiner

Primary Examiner—Robert L. Nasser
Assistant Examiner—Patricia C. Mallari
(74) Attorney, Agent, or Firm—Nixon Peabody LLP; Donald R. Studebaker

(57) ABSTRACT

The present invention relates to a method for determining the cardiac output of a subject by thermodilution measurements by providing a predetermined amount of thermal indicator in a blood vessel with the thermal indicator having a temperature different from the temperature of subject's blood, thus exhibiting an indicator temperature difference. By measuring the temperature of subject's blood at a second place downstream the cardiac output (CO) and the extravascular thermovolume can be determined as a function of the time for the thermodilution curve. As a function of the thermodilution curve the measurements of the amount of thermal indicator and/or thermal indicator volume temperature difference are adjusted to provide a more accurate determination of cardiac output.

7 Claims, 2 Drawing Sheets

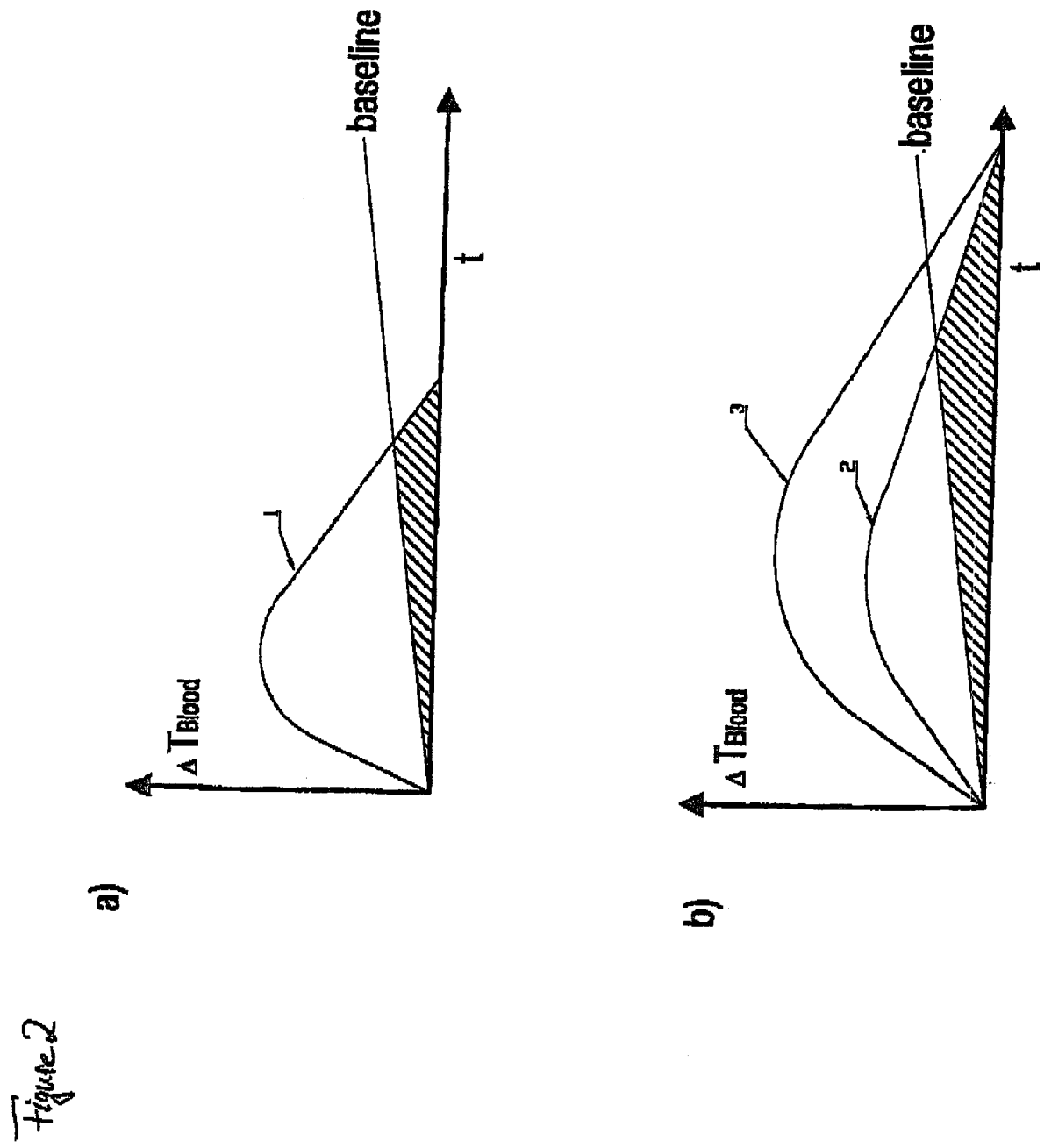

METHOD TO INCREASE TRANSPULMONARY THERMODILUTION CARDIAC OUTPUT ACCURACY BY USE OF EXTRAVASCULAR THERMOVOLUME TO CONTROL THE AMOUNT OF THERMAL INDICATOR

PRIORITY OF INVENTION

This application claims priority under 35 U.S.C. §119(e) from U.S. Provisional Application No. 60/161,931, filed Oct. 28, 1999.

FIELD OF THE INVENTION

The present invention relates to medical procedures and apparatus to perform medical procedures to determine the flow rate of blood. In particular, the invention relates to the determination of cardiac output characteristics for diagnosis purposes.

BACKGROUND OF THE INVENTION

The determination of cardiac output, or measurement of the blood volumetric output of the heart is substantially important for a variety of medical situations. Healthcare professionals utilize such information along with a number of additional pulmonary factors to evaluate the condition of their subject's heart. Even with the variety of approaches developed for measuring this output, each exhibit certain limitations and/or inaccuracies. The volumetric aspect of cardiac output provides information about the sufficiency of oxygen delivery to tissue or the oxygenation of the tissue. When used in combination with other measurements it provides important status and evaluation information of the cardiovascular system.

Methods for determining cardiac output as the thermodilution method are discussed, for example in U.S. Pat. Nos. 3,651,318, 4,217,910, and 4,236,527. As conventionally employed, this method involves either injecting a bolus of liquid into the bloodstream at a temperature which is cooler or warmer (usually cooler) than blood temperature, or heating a segment of the blood indirectly with electrical resistance heaters, and monitoring the temperature deviation of the blood as a function of time at a place downstream from the place at which the temperature deviation is caused. The area under the resulting temperature deviation vs. time curve (known as the thermodilution curve) is a measure of the rate at which the heart is pumping blood (usually expressed in liters per minute). If cardiac output is high, the area under the thermodilution curve will be relatively small in accordance with the well-known Stewart-Hamilton relationship. Conversely, if cardiac output is low, the area under the thermodilution curve will be relatively large.

Currently, the more accepted approach for deriving cardiac output values is an indicator dilution technique which takes advantage of refinements made earlier in pulmonary catheter technology. The standard of cardiac output measurement from pulmonary artery catheterization are described in for example, in U.S. Pat. Nos. 3,915,155, 3,726,269 and 3,651,318 involve periodic injection into the subject's bloodstream of a bolus, during which thermodilution measurements are performed to determine cardiac output. Such techniques cannot generally be used for continuous monitoring. Moreover, such catheterization techniques pose significant risk to the subject, including malignant arrhythmias, pulmonary artery rupture, and in rare cases, death. However since knowledge of cardiac output is crucial in the care of critically ill subjects, as well as subjects with chronic heart disease requiring monitoring of medication work has been underway to develop less invasive apparatus and methods for monitoring cardiac output.

Advances in the art now require only central venous and arterial catheters as opposed to such invasive methods. Additionally, processes and devices have been developed to determine the fill level of the circulatory system of a patient disclosed in WO93/21823. Additionally, WO93/21823 provides a process for determining the end diastolic heart volume, the pulmonary blood volume, the extravascular thermovolume and/or the global cardiac function index. Extravascular thermovolume correlates, if there is no significant perfusion defect in the lungs (e.g., pulmonary embolism), closely to the degree of extravascular lung water. However, the clinical value of that measurement has not been shown explicitly yet.

In a typical procedure, a cold bolus of saline at ice or room temperature in an amount of about 5–10 milliliters is injected through the catheter as a measurement procedure which will require about two minutes to complete. For purposes of gaining accuracy, this procedure is repeated three or four times and readings are averaged. Consequently, the procedure requires an elapsed time of 4–5 minutes. In general, the first measurement undertaken is discarded inasmuch as the catheter will have resided in the bloodstream of the body at a temperature of about 37° C. Accordingly, the first measurement procedure typically is employed for the purpose of cooling the dilution channel of the catheter, and the remaining measurements then are averaged to obtain a single cardiac output value. Thus, up to about 40 ml of fluid is injected into the intravascular system of the patient with each measurement which is undertaken. As a consequence, this procedure is carried out typically only one to two times per hour over a period of 24 to 72 hours. While practitioners would prefer that the information be developed with much greater frequency, the procedure, while considered to be quite accurate, will add too much fluid to the cardiovascular system if carried out too often.

Of course, the accuracy of the procedure is dependent upon an accurate knowledge of the temperature, volume, and rate of injection of the liquid bolus. Liquid volume measurements during manual infusions are difficult to make with substantial accuracy. For example, a syringe may be used for injecting through the catheter with the result that the volume may be identified only within several percent of its actual volume. Operator error associated with volume measurement and rate of injection also may be a problem. Because the pulmonary catheters employed are somewhat lengthy (approximately 30 to 40 inches), it is difficult to know precisely the temperature of the liquid injectate at the point at which it enters the bloodstream near the distal end of that catheter. Heat exchange of the liquid dispensing device such as a syringe with the catheter, and the blood and tissue surrounding the catheter upstream of the point at which the liquid is actually released into the blood may mean that the injectate temperature is known only to within about five percent of its actual temperature. Notwithstanding the slowness of measurement and labor intensity of the cold bolus technique, it is often referred to as the "gold standard" for cardiac output measurement by practitioners. In this regard, other techniques of determining cardiac output typically are evaluated by comparison with the cold bolus approach in order to determine their acceptability.

Another technique of thermodilution to measure cardiac output employs a pulse of temperature elevation as the indicator signal. In general, a heating coil is mounted upon the indwelling catheter so as to be located near the entrance of the heart. That coil is heated for an interval of about three seconds which, in turn, functions to heat the blood passing adjacent to it. As is apparent, the amount of heat which can be generated from a heater element is limited to avoid a thermocoagulation of the blood or damage to tissue in adjacency with the heater. This limits the extent of the signal which will be developed in the presence of what may be considered thermal noise within the human body. In this regard, measurement error will be a result of such noise phenomena because of the physiological blood temperature variation present in the body. Such variations are caused by respirations, coughing, and the effects of certain of the organs of the body itself. For further discussion see Afonzo, S., et al., "Intravascular and Intracardiac Blood Temperatures in Man," Journal of Applied Physiology, Vol. 17, pp 706–708, 1962 and U.S. Pat. No. 4,595,015.

This thermal noise-based difficulty is not encountered in the cold bolus technique described above, inasmuch as the caloric content of a cold bolus measurement is on the order of about 300 calories. By contrast, because of the limitations on the amount of heat which is generated for the temperature approach, only 15 or 20 calories are available for the measurement. Investigators have attempted to correct for the thermal noise problem through the utilization of filtering techniques, for example, utilizing moving averages over 6 to 12 readings. However, where such corrective filtering approaches are utilized, a sudden downturn in the hemodynamic system of a patient will not be observed by the practitioner until it may be too late. The effective measurement frequency or interval for this technique is somewhat extended, for example about 10 minutes, because of the inaccuracies encountered. In this regard, a cardiac output value is achieved only as a consequence of a sequence of numerous measurements. In general, the approach does not achieve the accuracy of the above-discussed cold bolus technique. Thermodilution techniques involving the use of electrical resistance heaters are described, for example, in U.S. Pat. Nos. 3,359,974, 4,217,910, 4,240,441 and 5,435,308.

Other approaches to the elimination of an injectant in thermodilution procedures have been, for example, to introduce the thermal signal into the flowing blood by circulating a liquid within the catheter, such liquid preferably being cooler than the blood temperature. See in this regard, U.S. Pat. No. 4,819,655. While, advantageously, no injectant is utilized with such procedure, the method has the disadvantage that only a limited thermal signal is available as compared with the cold bolus approach, and, thus, the measurement is susceptible to error due to physiological temperature variations. As another example, a technique has been proposed wherein a stochastic excitation signal present as a series of thermal pulses of varying duration is asserted within the bloodstream, and the resultant output signal downstream, now present as blood temperature variation, is measured. The blood flow rate then is extracted by cross-correlating the excitation signal and measured output signal. See U.S. Pat. No. 4,507,974.

The current state of the art in performing transpulmonary thermodilution measurements is to inject a bolus of thermal indicator. The used injectate volume in most application is 10 ml or, as a guideline, 0.15 ml/kg. Cardiac output is calculated from an arterial thermodilution curve in the usual way using the Stewart-Hamilton algorithm. For a cold bolus injection algorithms to derive the cardiac output are based on the Stewart-Hamilton equation:

$$CO = \frac{V_i(T_B - T_i)K_1 K_2}{\int \Delta T_B(t)dt}$$

where $T_B$ is the blood temperature, $T_i$ is the indicator temperature, $V_i$ is the indicator volume, $K_1$ and $K_2$ are constants to consider the specific measurement setup and $\Delta T_B(t)$ is the blood temperature as a function of time with respect to the baseline blood temperature $((T_B)$. To obtain cardiac output in liters per minute, the area under the thermodilution curve has to be integrated. Then the amount of extravascular thermovolume is computed via the determined cardiac output and the two parameters mean transit time (MTt) and exponential downslope time (DSt).

A typical, ideal transpulmonary thermodilution curve is shown in FIG. 1. In this example, the inverted blood temperature (the peak represents a colder blood temperature) after a cold bolus injection is presented. Using an indicator, warmer than the blood temperature results in a principally similar curve. Cardiac output (CO) is derived from the amount of indicator used and the area under the shown curve.

SUMMARY OF THE INVENTION

The present invention addresses the need for improved methods for determining the cardiac output of a subject by thermodilution measurements. As an advantage over the present state of the art the invention provides a method for increasing the accuracy of thermodilution measurements by means of biofeedback and adjustment.

In one embodiment of the invention, the information is obtained by providing a predetermined amount of thermal indicator in a blood vessel having a temperature different from the temperature of subject's blood, thus exhibiting an indicator temperature difference. A thermodilution curve is then determined by measuring the temperature of subject's blood at a second place downstream from the injection site as a function of time. Cardiac output (CO) is then determined from the thermodilution curve to provide the extravascular thermovolume. A new amount of thermal indicator and/or a new thermal indicator temperature difference can then be determined according to the new thermovolume. The process can then be repeated with the new amount of indicator and/or new indicator temperature difference to provide more accurate results.

In another embodiment, the invention also provides a means where the predetermined amount of thermal indicator is provided as an indicator liquid.

In another embodiment, the invention also provides for the cardiac output to be determined by transpulmonary thermodilution and when the extravascular thermovolume correlates to extravascular lung water volume. Extravascular thermovolume correlates, if there is no significant perfusion defect in the lungs (e.g., pulmonary embolism), closely to the degree of extravascular lung water. However, the clinical value of the measurement has not been shown explicitly yet.

In another embodiment, the invention also provides for the new amount of indicator and/or new indicator temperature difference to be increased or decreased according to the amount of said determined extravascular thermovolume.

In another embodiment, the invention also provides for the extravascular thermovolume to be determined from a mean transit time of said thermal indicator required by the thermal indicator to travel from the first place to the second place, from the downslope of the thermodilution curve and from the cardiac output.

Another embodiment of the invention provides an apparatus for determining the cardiac output of a subject by thermodilution measurements by providing a means of delivering at a first place a predetermined amount of thermal indicator in a blood vessel of the subject. The thermal indicator would have a temperature different from the temperature of subject's blood, to express an indicator temperature difference. Also, the apparatus provides a temperature sensor for measuring the temperature of subject's blood at a second place downstream of the first place as a function of time to determine a thermodilution curve. A computer is connected to the temperature sensor for determining cardiac output and an extravascular thermovolume from the thermodilution curve. The computer utilizes the measurements gathered and determines a new amount of indicator and/or a new indicator temperature difference according to the thermovolume. Then the computer controls and provides means of supplying a new amount of thermal indicator/temperature difference in the blood vessel and controls the temperature sensor to measure the temperature of subject's blood as a function of time at the second place.

In another aspect of the invention, the apparatus may utilize an injector as the means of delivery.

BRIEF DESCRIPTION OF THE FIGURES

FIGS. 2a and 2b represent schematically sketched transpulmonary curves with the same cardiac output (CO), but measured with different boundary conditions.

DETAILED DESCRIPTION OF THE INVENTION

Figure 1:
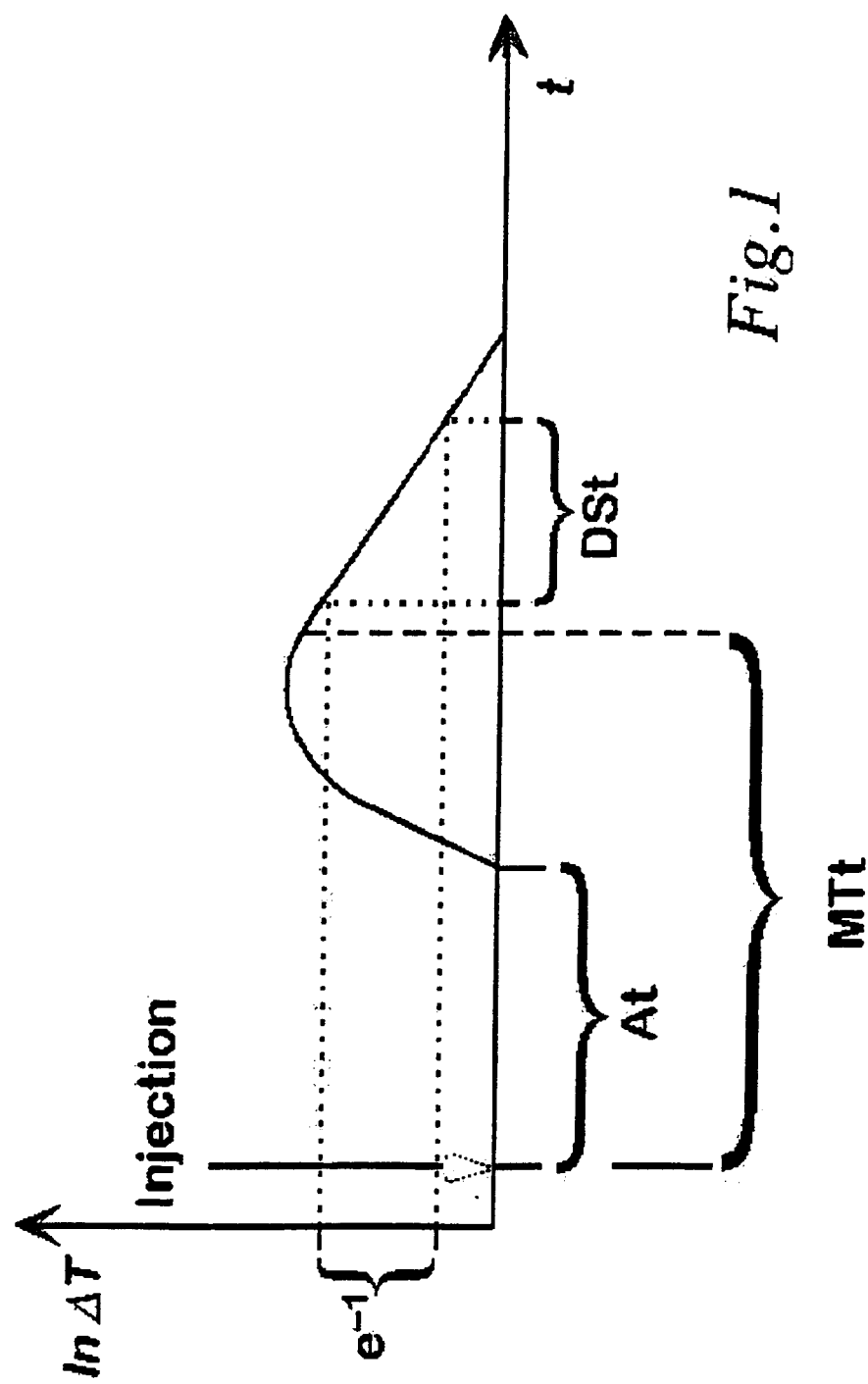
FIG. 1 represents a typical transpulmonary thermodilution curve.

The accuracy of transpulmonary thermodilution can be increased by taking the extravascular thermovolume into account in order to give a feedback and control for the amount of thermal indicator that has to be used. Thermal indicator in this context can either be a cold or warm (with respect to the blood temperature) bolus injection or a supply of the thermal indicator over a defined time interval.

FIG. 1 represents a typical transpulmonary thermodilution curve. Depicted is an inverted blood temperature curve after the injection of a cold bolus. Characteristic time intervals that can be derived from the curve include the time from injection to the initial curve incline denoted as the appearance time (At), the mean transmit time (MTt), which is the time from injection to the vertical centroid line of the curve, representing the statistical mean of the transit time distribution, and the exponential downslope time (DSt) representing the time the curve takes to drop by the factor $e^{-1}$ in the stage of exponential decay.

In FIG. 2 several schematically sketched transpulmonary thermodilution curves with the same, constant cardiac output (CO), but measured with different boundary conditions are presented. Additionally, for the purpose of illustration an excessive baseline drift of the blood temperature is shown. Curve 1 in FIG. 2a represents a measurement done with a certain amount of thermal indicator and with no further extravascular thermovolume present. The hatched area illustrates the error of the area under the blood temperature curve and thus potential error in CO which is introduced due to the baseline drift. Analogous, Curve 2 in FIG. 2b represents a measurement with the same amount of thermal indicator which results in the same CO. However, due to the extravascular thermovolume, the peak in the blood temperature change is less pronounced and the curve is broader. Curve 2 still has the same area and thus the same CO as Curve 1, but the potential error due to the baseline drift is significantly larger resulting in a less reliable CO determination. Using twice the amount of thermal indicator results in Curve 3 which, with respect to Curve 2, has twice the area under the blood temperature curve for constant CO (compare the Stewart-Hamilton equation for constant CO). It can be seen that the potential error due to the baseline drift is significantly less in Curve 3 as compared to Curve 2.

The cardiac output of a subject can be determined by thermodilution measurements which include supplying a known amount of thermal indicator, which is at a temperature different from the temperature of the subject's blood, in a blood vessel of said subject. The difference is exhibited as an indicator temperature difference. By measuring the temperature of subject's blood at a second place downstream of the first place a thermodilution curve is determined as a function of time. Following a determination of cardiac output and an extravascular thermovolume from the thermodilution curve a new amount of thermal indicator and/or a new thermal indicator temperature can be adjusted according to the thermovolume. By repeating the supply of a known amount of thermal indicator at the first place using the new amount of indicator and/or new indicator temperature difference and taking measurements at the second place a more accurate and reliable result of cardiac output may be determined.

The method as described above may also utilize a predetermined amount of thermal indicator supplied as an indicator liquid. When determining the cardiac output utilizing the described transpulmonary thermodilution method the extravascular thermovolume accounted for may correlate to extravascular lung water. Extravascular thermovolume correlates, if there is no significant perfusion defect in the lungs (e.g., pulmonary embolism), closely to the degree of extravascular lung water. However, the clinical value of the measurement has not been shown explicitly yet. As a result the new amount of indicator and/or new indicator temperature difference may be increased or decreased according to the amount of extravascular thermovolume determined by previous supply of indicator or other techniques. The amount of extravascular thermovolume can be determined from the parameters mean transmit time, cardiac output and exponential downslope time.

An apparatus for determining the cardiac output of a subject by thermodilution measurements may comprise a means for supplying at the first place a predetermined amount of thermal indicator in a blood vessel of the subject. The thermal indicator temperature being different from the temperature of subject's blood to exhibit an indicator temperature difference. The apparatus provides a temperature sensor for measuring the temperature of subject's blood at a second place downstream of said first place to determine the thermodilution curve as a function of time. The apparatus may have a computer connected to the temperature sensor for determining cardiac output and extravascular thermovolume from the thermodilution curve. The computer may be utilized for determining a new amount of indicator and/or a new indicator temperature difference according to said thermovolume by measurement provided from the thermodilution curve, cardiac output and extravascular thermovolume measurements. The apparatus and computer provide a means for controlling and supplying a new amount of thermal indicator/temperature difference into the blood vessel and controlling the temperature sensor to measure the temperature of subject's blood as a function of time at said second place. The apparatus may also include a means for including an injector for delivery of the thermal indicator or other providing means include an injector.

The new method to increase the accuracy of transpulmonary thermodilution cardiac output measurements is based on the estimation of the amount of extravascular thermovolume from the first performed thermodilution measurement and then trigger a feedback to control the amount of thermal indicator used in following thermodilution measurements. Having a device which in certain time intervals, automatically supplies the required thermal indicator further allows this method to be used to control the amount of thermal indicator in cases where the extravascular thermal volume changes.

What is claimed is:

1. A method for determining the cardiac output of a subject by thermodilution measurements comprising the steps of:
   a) providing at a first place a predetermined amount of thermal indicator in a blood vessel of said subject, said thermal indicator having a temperature different from the temperature of subject's blood, thus exhibiting an indicator temperature difference;
   b) measuring the temperature of subject's blood at a second place downstream of said first place as a function of time to determine a thermodilution curve;
   c) determining cardiac output and an extravascular thermovolume from said thermodilution curve;
   d) determining a new amount of thermal indicator and/or a new thermal indicator temperature difference according to said thermovolume;
   e) repeating steps a), b), c) using said new amount of indicator and/or new indicator temperature difference.

2. The method as claimed in claim 1, wherein said predetermined amount of thermal indicator is provided as an indicator liquid.

3. The method as claimed in claim 1, wherein said cardiac output is determined by transpulmonary thermodilution and said extravascular thermovolume correlates to extravascular lung water volume.

4. The method as claimed in claim 1, wherein said new amount of indicator and/or new indicator temperature difference is increased according to the amount of said determined extravascular thermovolume.

5. The method as claimed in claim 1, wherein said extravascular thermovolume is determined from a mean transit time of said thermal indicator required by said thermal indicator to travel from said first place to said second place, from downslope of said thermodilution curve and from said cardiac output.

6. An apparatus for determining the cardiac output of a subject by thermodilution measurements comprising:
   a) providing means for providing at a first place a predetermined amount of thermal indicator in a blood vessel of said subject, said thermal indicator having a temperature different from the temperature of subject's blood, thus exhibiting and indicator temperature difference;
   b) a temperature sensor for measuring the temperature of subject's blood at a second place downstream of said first place as a function of time to determine a thermodilution curve;
   c) a computer connected to said temperature sensor for determining cardiac output and an extravascular thermovolume from said thermodilution curve, and determining a new amount of indicator and/or a new indicator temperature difference according to said thermovolume, and controlling said providing means to provide said new amount of thermal indicator/ temperature difference in said blood vessel and controlling said temperature sensor to measure the temperature of subject's blood as a function of time at said second place.

7. Apparatus as claimed in claim 6, wherein said providing means include an injector.

* * * * *